United States Patent [19]

Dolan et al.

[11] Patent Number: 4,752,761
[45] Date of Patent: Jun. 21, 1988

[54] THERMO-ELECTRICALLY REGULATED ADSORPTIVE SENSING METHOD AND APPARATUS

[76] Inventors: James P. Dolan; Patrick M. Dolan, both of 4119 N.E. 96th St., Seattle, Wash. 98115

[21] Appl. No.: 891,153

[22] Filed: Jul. 31, 1986

[51] Int. Cl.⁴ ............................................. H01L 7/00
[52] U.S. Cl. ...................................... 338/34; 338/13; 73/23; 73/26; 29/592 R
[58] Field of Search ................. 338/13, 34, 35; 73/23, 73/25, 27 R, 26, 29, 73; 324/71.5, 71.1; 340/517; 219/462, 531, 540; 29/592 R

[56] References Cited

U.S. PATENT DOCUMENTS

| | | | |
|---|---|---|---|
| 2,904,406 | 9/1959 | Moore | 23/232 |
| 3,045,198 | 7/1962 | Dolan et al. | 338/13 |
| 3,893,230 | 7/1975 | Stadler et al. | 29/592 |
| 3,906,473 | 9/1975 | LeVine | 340/237 R |
| 3,932,807 | 7/1976 | Wilson | 324/71 SN |
| 4,112,356 | 9/1978 | Toy | 324/71 SN |
| 4,129,030 | 12/1978 | Dolan | 73/73 |
| 4,224,595 | 9/1980 | Dolan | 338/34 |
| 4,237,721 | 12/1980 | Dolan | 73/23 |
| 4,361,027 | 11/1982 | Schmitt | 73/23 |
| 4,441,356 | 4/1984 | Bohl | 73/23 |
| 4,453,397 | 6/1984 | Ohta | 73/23 |

FOREIGN PATENT DOCUMENTS 1125858  6/1982  Canada .

OTHER PUBLICATIONS

Cambion ®, *Temperature Control by CAMCOOL TM Thermoelectrics*—Catalog 300 (copyrighted 1982).
Cambion ®, *Thermoelectric Devices Application Notes* (copyrighted 1980).
Thermometrics Inc., *Thermistors*—Catalog No. 181-D (undated).

Primary Examiner—E. A. Goldberg
Assistant Examiner—M. Lateef
Attorney, Agent, or Firm—Graybeal, Jensen & Puntigam

[57] ABSTRACT

A thermo-electrically regulated adsorptive sensing device comprising a gas adsorptive sensing element having a stratum of adsorbently sensitive particles, a thermistor for sensing the temperature of the sensing element, a thermo-electric module for controlled cooling and heating of the sensing element, a heat sink, and a controller unit for applying variable amounts of electrical current through the thermo-electric module to appropriately heat or cool the sensing element in a rapid, controlled and accurate fashion. The thermo-electric module may be operated either to maintain the stratum of particles of the sensing element within about 1° (0.6° C.) of the optimal sensing temperature or operated to heat the particles in a controlled fashion to a relatively high purging temperature at which the gas is relatively rapidly desorbed, and then cool the particles in a controlled fashion to a relatively lower sensing temperature at which the gas is relatively rapidly adsorbed by the particles.

15 Claims, 2 Drawing Sheets

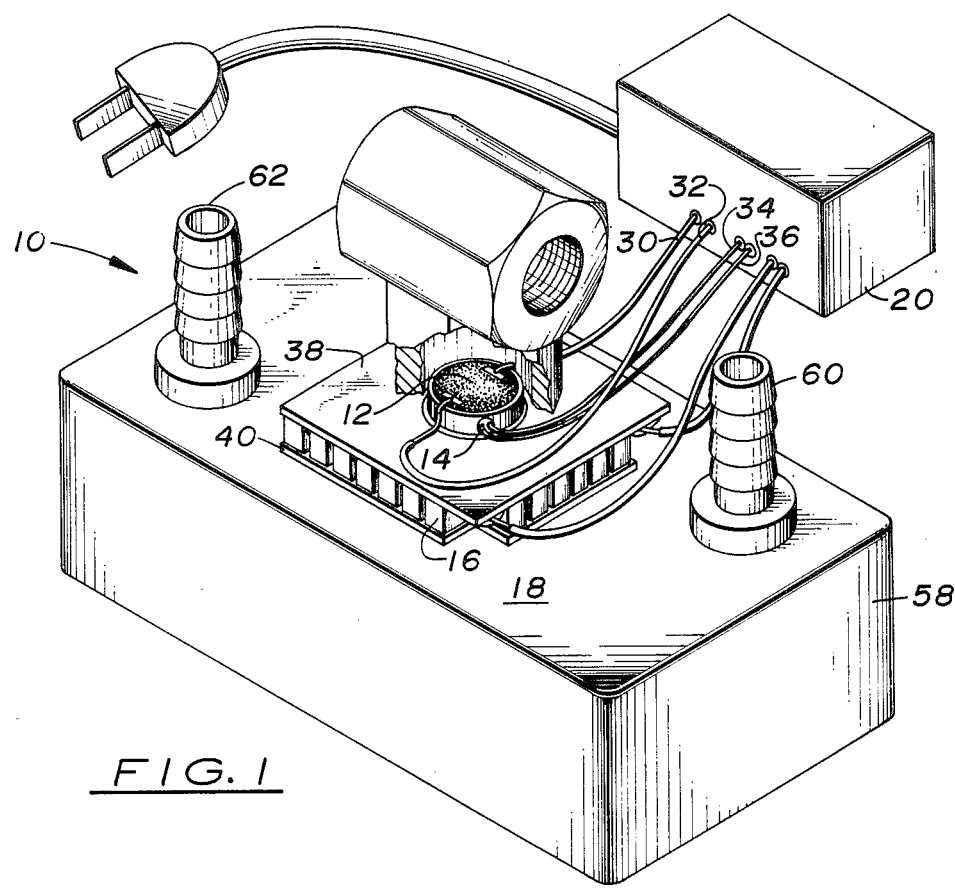
FIG. 1
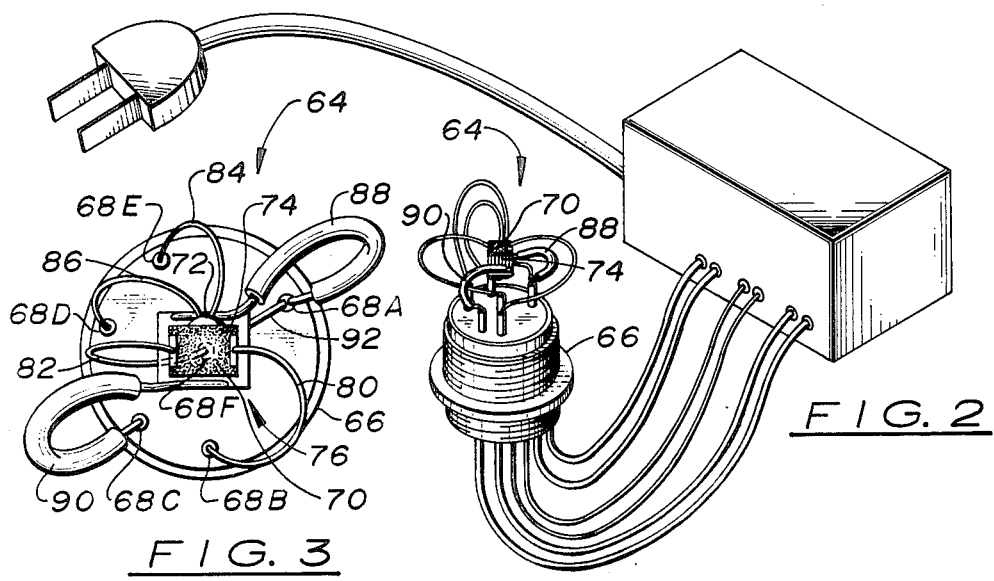
FIG. 2
FIG. 3

THERMO-ELECTRICALLY REGULATED ADSORPTIVE SENSING METHOD AND APPARATUS

BACKGROUND OF THE INVENTION

1. Technical Field

This invention relates to sensors for indicating concentrations of liquids, vapors, gases and the like, and more particularly to a thermo-electrically regulated adsorptive sensing method and an adsorptive sensing device usable therewith.

Accurate and rapid detection of concentrations of liquids, vapors, gases and the like is necessary in a great many industrial, medical, safety and other applications. For instance, safe yet effective medical anesthesia requires accurate, continuing and rapidly responsive indication of the concentration of anesthetic in the gas mixture inhaled by the patient. Relatively small increases or decreases in concentration of the anesthetic often require immediate corrective response from attending medical personnel. If such response is delayed, such as by failure to detect the change in anesthetic concentration, the success of the medical procedure can be endangered and the patient's life may be placed at risk. Optimal performance of a medical anesthetic sensor is characterized by high sensitivity to and accurate indication of relatively small increases and decreases in concentration of the anesthetic. Many other applications for sensing devices require comparable sensitivity, accuracy and response time.

2. Description of the Prior Art

Dolan U.S. Pat. No. 3,045,198, issued July 17, 1962, discloses an adsorptive sensing element having a stratum of exposed, electrically conductive, discrete, adsorbent particles anchored on the non-conductive nonabsorbent resilient surface of a base. The particles are anchored such that under normal conditions adjacent particles are in conductive contact whereby at least one but usually many electrical paths extend across the stratum between spaced apart electrical leads, each such lead contacting a broad portion of the stratum. Exposure of the adsorptive element to a selected substance to be detected causes a portion of such substance to be adsorbed onto the surfaces of the particles, increasing the resistance of or reducing the current flow through the path or paths between the electrical leads of the adsorptive element. Dolan U.S. Pat. No. 4,129,030 discloses sensing apparatus including an adsorptive sensing element placed in a balanced bridge circuit for detection of small changes in the resistance of or the current flow through the adsorptive sensing element. Dolan U.S. Pat. No. 4,224,595 discloses an adsorptive sensing element having various sized abutting adsorbent particles for increasing the sensitivity of the adsorptive element. Dolan U.S. Pat. No. 4,237,721 discloses sensing apparatus including an adsorptive sensing element operated in its non-linear region for sensing substances having a Van der Waals' "a" constant of 9 or less, and a balanced bridge circuit for detecting changes in the resistance of or the current flow through the adsorptive element.

Adsorptive sensing elements display an inherent hysteresis effect, responding more rapidly to increases in the concentration of the substance of interest than to decreases therein. This hysteresis effect results because the adsorptive particles desorb portions of the substance more slowly than they adsorb the substance. Adsorptive sensing elements are also temperature sensitive, having greater sensitivity at lower temperatures.

Le Vine U.S. Pat. No. 3,096,473 discloses a method for operating a gas sensor which exhibits substantial response to contact adsorption by a given class of gases, in which the sensor is alternately operated at a lower sensing temperature to sense said gases and at a higher purging temperature to purge the sensor of such gases. Le Vine relies on passive cooling, presumably through radiation, convection and conduction, to return the adsorptive element from the higher purging temperature to the lower sensing temperature. The time required for the adsorptive element to return to the lower temperature determines the sampling rate of the sensor, and thus the minimum achievable response time of the sensor to changes in concentration of the gas. The Le Vine sensor is thus not suited to applications where changes in concentration can occur faster than the adsorptive element can be first heated and then passively cooled.

SUMMARY OF THE INVENTION

It is an object of the present invention to provide an adsorptive-type sensing device having a sensing element which can be rapidly cooled and heated in a controlled fashion.

It is a further object of this invention to provide a method for operating a thermo-electrically regulated adsorptive sensing device by which the sensing element thereof may be readily and accurately maintained substantially at a selected temperature.

It is another object of this invention to provide a method for operating a thermo-electrically regulated adsorptive sensing device in controlled adsorb/purge cycles in which the sensing element of the device is rapidly cycled between relatively higher purging temperatures and relatively lower sensing temperatures.

It is yet another object of this invention to provide a small, highly accurate, reliable and completely electronic adsorptive sensing device.

These and other objects are provided by a thermo-electrically regulated adsorptive sensing device comprising: a sensing element which exhibits substantial response to adsorption of the substance of interest when the temperature of the is in a lower range, and which purges itself of said adsorbed substance when operated in a temperature range higher than said lower range; temperature sensing means for sensing the temperature of the stratum of particles; and temperature regulating means for controlled cooling and heating of the stratum of particles.

The above objects are further provided by a method for operating an adsorptive sensing device comprising the steps of: exposing to a selected substance of interest a sensing element including a base having a non-adsorbent, electrically non-conductive resilient surface, a stratum of discrete, exposed, electrically conductive particles adsorbently sensitive to a selected substance of interest, said particles being independently anchored on the surface of the base such that electrically conductive contact normally exists between adjacent particles substantially fully throughout the stratum of particles, and two sensor output leads in electrically conductive contact with the stratum of particles at separated points thereon; controlled heating of the stratum of particles until the stratum of particles reaches a relatively higher purging temperature at which the substance of interest is relatively rapidly desorbed from said particles; controlled cooling of the stratum of particles until the stratum of particles reaches a relatively lower sensing temperature at which the substance of interest is relatively rapidly adsorbed by said particles; and measuring the electrical resistance or conductance between the sensor output leads when the stratum of particles is substantially at the sensing temperature.

Other features and advantages of the present invention will become apparent from the following detailed description of a typical embodiment thereof, taken in conjunction with the accompanying drawings.

BRIEF DESCRIPTION OF THE DRAWINGS

FIG. 1 is an isometric view of a first embodiment of a sensor according to the present invention, showing the adsorptive sensing element, the thermistor, the thermo-electric module and the water cooled heat sink.

FIG. 2 is an isometric view of a second, miniaturized embodiment of a sensor according to the present invention, showing the miniature adsorptive sensing element, the miniature thermistor, and the miniature thermo-electric module all integrally mounted on a modular socket, drawn to the same scale as FIG. 1.

FIG. 3 is an enlarged plan view of the sensor of FIG. 2.

DESCRIPTION OF THE PREFERRED EMBODIMENTS

First Embodiment—Full-Scale Sensing Device

Figure 4:
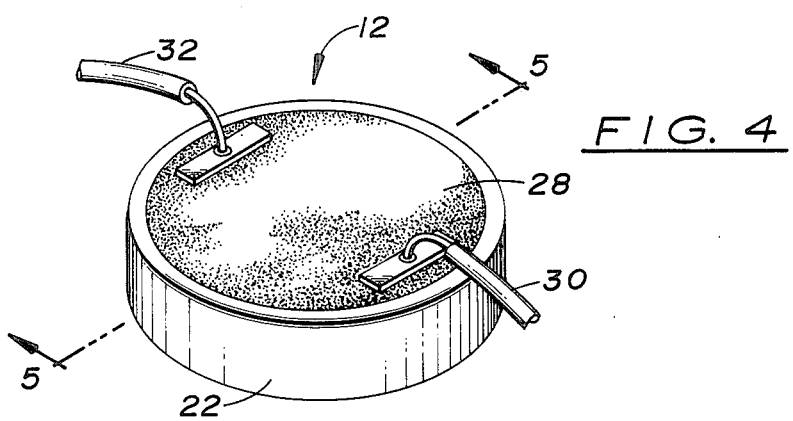
FIG. 4 is an isometric view of the adsorptive sensing element of FIG. 1.
Figure 5:
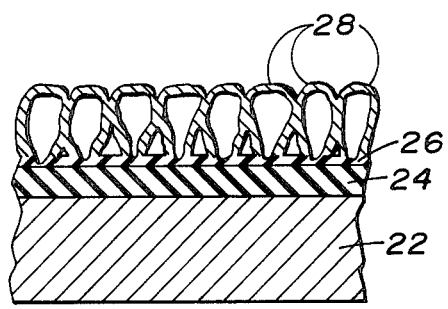
FIG. 5 is a partial vertical cross-sectional view of the adsorptive particles of the adsorptive sensing element of FIG. 1, taken along the line 5—5 of FIG. 4.

As best seen in the isometric view of FIG. 1, the sensor system 10 of the present invention comprises a sensing element 12, a thermistor 14, a thermo-electric module 16 and heat sink 18, and a control and power unit 20. As best seen in FIGS. 4 and 5, the sensing element 12 is an adsorptive-type sensing element substantially as disclosed in Dolan U.S. Pat. No. 3,045,198. The sensing element 12 comprises a non-conductive, non-absorbent substantially rigid cylindrical base 22, a non-conductive resilient substrate 24, a resilient adhesive layer 26, a stratum of exposed, electrically conductive, discrete adsorbent particles 28, and two electrical sensor output leads 30,32. The resilient substrate 24 comprises a flat circular element fixedly attached by a lower surface thereof to an upper surface of the base 22. The particles 28 are fixedly anchored to an upper surface of the resilient substrate 24 by the adhesive layer 26. The sensor output leads 30,32 are fixedly and conductively attached to a portion of the stratum of particles 28, and are spaced apart across the stratum of particles. The particles 28 are anchored to the resilient substrate 24 such that under normal conditions adjacent particles are in conductive contact whereby at least one but usually many electrical paths extend across the stratum of particles between the sensor output leads 30,32. The particles 28 are suitably selected such that exposure of the particles to a selected substance to be detected causes a portion of such substance to be adsorbed onto the surfaces of the particles, increasing the resistance or decreasing the conductance through the electrical path or paths through the stratum of particles between the sensor output leads 30,32. Such changes in resistance or conductance can be readily converted by suitable electrical circuitry into a visual, audible or other display of the presence and concentration of the substance of interest.

The thermistor 14 is fixedly and thermally conductively attached to the cylindrical surface of the base 22 of the sensing element 12 so as to accurately measure the temperature of the particles 28. The thermistor 14 is suitably a conventional thermally sensitive resistor which exhibits a change in electrical resistance with a change in the temperature of the thermistor. Two thermistor output leads 34,36 extend from the thermistor 14 to the sensor control unit 20 for ready measurement of the resistance through the thermistor, and thus of the temperature of the sensing element 12.

The sensing unit 12 and attached thermistor 14 are mounted on a source side 38 of the thermo-electric module 16 for controlled cooling and heating of the sensing element. A sink side 40 of the thermo-electric module 16 is fixedly and thermally conductively attached to the heat sink 18. The thermo-electric module 16 transfers heat from either the source side 38 to the sink side 40, or vice versa, depending on the direction of the electrical current flowing through the module. The thermo-electric module 16 allows rapid and precisely controlled cooling and heating of the sensing element 12 by selectively applying electrical current through the module.

Figure 6:
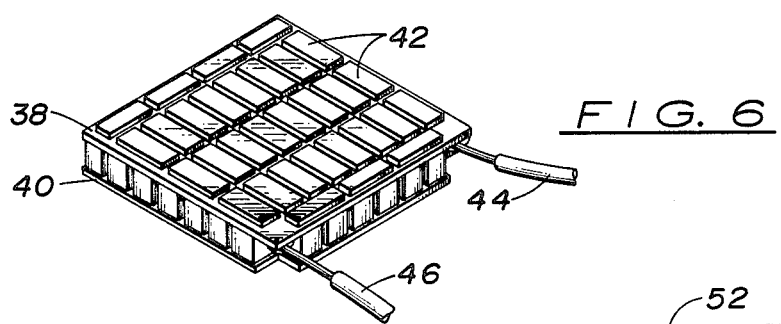
FIG. 6 is an isometric view of the thermo-electric module of FIG. 1.
Figure 7:
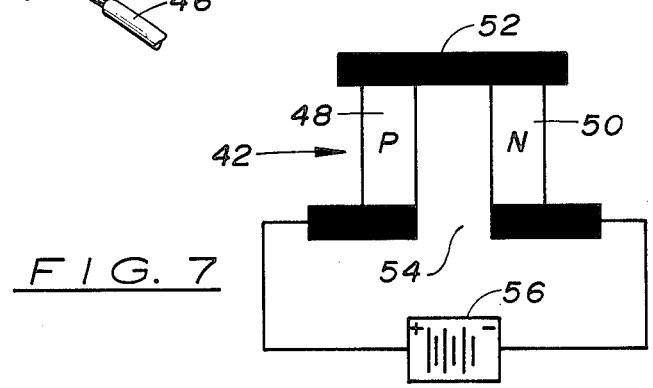
FIG. 7 is a schematic view of a single thermo-electric couple of the thermo-electric module of FIG. 6.

As shown in FIG. 6, the thermo-electric module 16 comprises a plurality of discrete thermo-electric couples 42 sandwiched between the source side 38 and the sink side 40 of the module, and two thermo-electric input leads 44,46. As seen in FIG. 7, each thermoelectric couple 42 comprises a P-type semi-conducting element 48 and an N-type semi-conducting element 50. Upper ends of the P- and N-type semi-conductors of each thermo-electric couple are thermally conductively attached to the source side 38 of the thermo-electric module 16, and are electrically connected in series to create a first junction 52 of a P-N couple. The second junction 54 of the P-N couple is formed between the lower ends of the semi-conductors 48,50, which are connected through an electrical current source 56 by the thermo-electric module input leads 44,46. It is a characteristic of P-N semi-conductor couples that electric current flowing through the couple in a first direction causes heat to be absorbed at the first junction 52 of the couple and rejected at the second junction 54. In other words, the P-N couple acts as a heat pump, cooling the first junction 52 and heating the second junction 54. If the electrical current is reversed the flow of heat is reversed as well, heating the first junction 52 and cooling the second junction 54. The plurality of thermo-electric couples 42 comprising the thermo-electric module 16 are arranged to be capable of pumping a predetermined maximum design heat flow from the sensing element 12 to the heat sink 18, or vice versa. Said maximum design heat flow of the sensor 10 is determined with reference to the anticipated temperature of the substance or substances of interest, the range and frequency of temperature cycles to be imposed on the sensing element 12, the power requirements of the thermo-electric module 16, and the ambient temperature surrounding the sensor 10.

The thermo-electric module 16 is particularly well suited to controlled cooling and heating of the sensing element 12 of the present invention. Thermo-electric modules are relatively smaller and lighter than other heat pumping devices. The complete absence of moving parts in thermo-electric modules greatly increases their reliability. Being solid-state devices, thermo-electric modules are easily and accurately controlled electronically, and have convenient power requirements. The sensor 10 of the present invention, having a thermoelectric module 16 in combination with an adsorptive sensing element 12 and a conventional thermistor 14 provides a small, highly responsive, accurate, reliable and completely electronic adsorptive sensor for indicating concentrations of gases, vapors, liquids and the like.

The heat sink 18 is provided because the thermo-electric module 16 merely pumps heat to and from the sensing element 12, and thus requires a reservoir into which excess heat can be dumped, and from which additional heat can be drawn. The heat sink 18 is fixedly and thermally conductively attached to the sink side 40 of the thermo-electric module 16. The heat sink 18 is typically sized with reference to the maximum design heat flow into the sink side 40 of the thermo-electric module 16. The heat sink 18 shown in FIG. 1 is a relatively high capacity, liquid-cooled heat sink having a substantially hollow enclosed circulation chamber 58, a liquid supply fitting 60 and a liquid return fitting 62. In use, the liquid supply fitting 60 is connected to a source of flowing liquid such as tap water, and the liquid return fitting 62 is connected to a return or drain for such liquid. Liquid passing from the liquid supply fitting 60 through the heat sink 18 to the liquid return fitting 62 is mixed and circulated in the circulation chamber 58. When the thermo-electric module 16 is operated to cool the sensing element 12, heat pumped to the sink side 40 of the module is thermally conducted through the heat sink 18 to the liquid, and is disposed of as the liquid is drained from the heat sink. Similarly when the operation of the thermo-electric module 16 is reversed to heat the sensing element 12, heat pumped into the sensing element is made up using heat extracted from the circulating liquid and thermally conducted through the heat sink to the sink side. The liquid cooled heat sink 18 provides the sensor 10 of the present invention with the widest possible range of ambient temperatures in which the sensor can be operated. In operating conditions where the maximum design heat flow of the sensing device is smaller, a lower capacity heat sink such as a forced or ambient air convection cooled heat sink may be provided instead of a liquid-cooled heat sink.

The operation of the thermo-electric module 16 is controlled by the control and power unit 20. Control circuitry contained within the control unit 20 applies current through the input leads of the thermo-electric module 16 in an appropriate direction to draw heat from or pump heat to the sensing element 12 as required for operation of the sensor 10. The temperature of the sensing element 12 is measured as the electrical resistance through the thermistor 14, said resistance being supplied to the control unit 20 by the thermistor output leads 34,36. When the sensor 10 is operated in a "controlled constant temperature mode", the control unit 20 applies current to the thermo-electric module 16 in negative feedback response to the output of the thermistor 14, so as to maintain the sensing element 12 at a constant temperature. When the sensor is operated in a "controlled adsorb/purge cycle mode", the control unit 20 alternately applies current through the thermoelectric module 16 in a first direction to heat the sensing element 12 to a higher purging temperature, and then in an opposite direction to cool the sensing element in a rapid and controlled fashion to a lower sensing temperature. The duration and/or magnitude of the current applied through the thermo-electric module 16 by the control unit 20 in the heating and cooling portions of the controlled adsorb/purge cycles can be determined by the control unit in response to a timing signal. Additionally or alternatively, the duration and/or magnitude of the heating and cooling portions can be determined by the control unit 20 in response to the output of the thermistor 14, so that the sensing element 12 is accurately and efficiently heated to the purging temperature and cooled to the sensing temperature. When the sensor 10 is operated in an "analytic mode" for sensing the composition of unknown gases, the current applied through the thermo-electric module 16 may be determined as in the controlled adsorb/purge mode, or it can be additionally controlled in response to the output of the sensing element as necessary to accurately analyze the unknown gases.

The control unit 20 preferably also receives and processes the output signal of the sensing element 12, although this signal can also be supplied directly to a processing device external to the sensor 10.

Second Embodiment—Miniature Sensing Device

Before discussing methods of using thermo-electrically regulated adsorptive sensing devices, it is instructive to consider a miniature second embodiment 64 of a sensor assembly according to the present invention, shown in FIGS. 2 and 3. The second sensor assembly 64 is a highly miniaturized device mounting all of the elements of a thermo-electrically regulated adsorptive sensing device on a small modular socket. The second sensor assembly 64 comprises a substantially conventional modular socket 66 having six pin-type electrical contacts 68A,68B,68C,68D,68E,68F arranged on an upper surface of the socket and extending therethrough so as to be connectable to conventional electrical conductors. A miniature sensing element 70, a miniature thermistor 72, a miniature thermo-electric module 74 and a miniature ambient cooled heat sink 76 are mounted above the upper surface of the socket 66 and electrically connected to the pins 68A,68B,68C,68D,-68E,68F thereof. A control unit 78 is suitably connected by conventional electrical conductors to the pins 68A,68B, 68C,68D,68E,68F of the socket 66.

The miniature sensing element 70 is substantially the same as the sensing element 12 of the first embodiment, including a stratum of adsorbent particles having one or more electrically conductive paths between spaced apart miniature sensor output leads 80,82. The miniature sensor output leads 80,82 are connected to a selected first pair of pins 68B,68F of the socket 66. The miniature thermistor 72 is fixedly and thermally conductively attached to the miniature sensing element 70 so as to accurately measure the temperature of the stratum of adsorbent particles. The thermistor output leads 84,86 of the miniature thermistor 72 are connected to a selected second pair of pins 68D,68E of the socket 66.

The miniature sensing element 70 is fixedly and thermally conductively attached to the source side of the miniature thermo-electric module 74. The miniature thermo-electric module 74 comprises eight thermoelectric couples arranged in two rows of four couples each and extending between the source side of the miniature thermo-electric module and the sink side thereof. Two input leads 88,90 of the miniature thermo-electric module 74 extend from the sink side of the module to the third pair of pins 68A,68C of the socket 66. It will be noted that the input leads 88,90 of the miniature thermoelectric module 74 are of substantially greater current capacity than the sensor output leads 78,80 or the thermistor output leads 84,86 of the miniature thermistor 72.

The miniature thermo-electric module 74 requires significantly less electrical power than the thermoelectric module 16 of the sensor 10 of the first embodiment. Thus, the miniature heat sink 76 can accommodate the heat flows produced by the miniature thermoelectric module 74 solely by means of ambient cooling. The miniature heat sink 76 comprises only a small thin rectangular plate of thermally conductive metal, such as copper, having an upper surface fixedly and thermally conductively attached to the sink side of the miniature thermo-electric module 74. A single uninsulated conductive support 92 extends from the lower surface of the miniature heat sink 76 to a selected pin 68A of the socket 66. The support 92 carries the assembly comprising the miniature sensing element 70, thermistor 72, thermo-electric module 74 and heat sink 76 spaced upwardly from the pins 68A,68B,68C,68D,68E,68F of the socket 66. The support 92 also conducts and dissipates excess heat from the miniature heat sink 76, as do the input leads of the miniature thermo-electric module 74. The second miniature sensor assembly 64 thus requires no separate cooling system, rendering it well suited to use where larger liquid cooled sensors would be inappropriate.

The following examples of methods of operation of thermo-electrically regulated adsorptive sensing devices are offered to more fully and completely illustrate the features and advantages of the present invention. While the examples are described with reference to the sensor 10 of the first embodiment, it will be understood that the methods of the present invention are also applicable to the miniature sensor 64 of the second embodiment and to other adsorptive sensing devices capable of controlled cooling and heating of the sensing elements thereof. It will also be understood that the substance of interest to be sensed using the methods of the present invention may be a gas, a vapor or a liquid.

EXAMPLE 1

Controlled Constant Temperature Method

A first method of operating the thermo-electrically regulated adsorptive sensor 10 to measure the concentration of a selected substance of interest involves maintaining the sensor as a relatively constant selected temperature by operation of the thermo-electric module 16 in response to negative feedback from the thermistor 14. It is a characteristic of adsorptive sensing elements that their sensitivities are greatest at some optimal temperature. These optimal sensing temperatures vary depending on the nature of the substances of interest and the characteristics of the sensing elements. Once the optimal sensing temperature has been selected, a maximum acceptable range of variation around such selected temperature is chosen, thereby determining upper and lower limit temperatures for the sensing element 12. The upper and lower limit temperatures are preferably very close to the optimal sensing temperature, so that the temperature of the sensing element 12 does not significantly vary from the optimal sensing temperature. The thermo-electrically regulated sensor 10 of the present invention can be extremely precisely controlled, such that the temperature of the sensing element 12 varies from the optimal sensing temperature by no more than $\pm 1.0°$ F. ($\pm 0.6°$ C.).

The "controlled constant temperature method" requires exposing the sensor 10 to an environment containing an unknown concentration of a selected substance of interest. The temperature of the sensing element 12 is measured by measuring the resistance through the thermistor 14. When the resistance through the thermistor 14 indicates that the temperature of the sensing element 12 exceeds the optimal sensing temperature by more than the permissible amount, i.e. is hotter than the upper limit temperature, the control unit 20 applies current through the thermo-electric module 16 in a selected direction so as to cause the thermo-electric module to draw heat from the sensing element 12 and dissipate said heat into the heat sink 18, thereby cooling the sensing element in a controlled fashion. Similarly, when the resistance through the thermistor 14 indicates that the temperature of the sensing element 12 is cooler than the lower limit temperature, the control unit 20 applies current through the thermo-electric module 16 in an opposite direction so as to cause the thermo-electric module to draw heat from the heat sink 18 and transfer the heat to the sensing element, thereby heating the sensing element in a controlled fashion. The concentration of the substance of interest is determined by measuring the electrical resistance or conductance between the sensor output leads 30,32. The concentration of the substance of interest can thus be measured continuously or periodically while the sensing element is maintained within a significantly narrower range around the optimal sensing temperature than heretofore possible using methods in which controlled heating and cooling are not employed.

The controlled constant temperature method of the present invention is well suited to initially detecting the presence of a substance of interest, where there is little chance of the adsorbent particles becoming saturated and reducing the sensitivity of the sensing device.

EXAMPLE 2

Controlled Adsorb/Purge Cycle Method

The hysteresis effect in adsorptive sensing devices can be minimized by cycling the adsorptive element of the device between a selected lower sensing temperature at which the element's sensitivity to the substance of interest is high, and a relatively higher purging temperature at which the adsorbed substance is driven off from the particles of the sensing element. A single such complete cycle of cooling and heating may be termed an "adsorb/purge cycle." The present invention provides a superior method of operating an adsorptive sensor 10 using adsorb/purge cycles, by providing both controlled cooling and controlled heating of the sensor by means of the thermo-electric module 16. The rapid controlled cooling radically shortens the time required to complete one adsorb/purge cycle, and thus significantly improves the sensor's response time to changes in the concentration of the substance of interest.

The "controlled adsorb/purge cycle method" of the present invention requires exposing the sensor 10 to an environment containing an unknown concentration of a selected substance of interest. The stratum of particles of the adsorptive sensing element 12 is cooled in a controlled fashion to a lower sensing temperature at which the substance of interest is relatively rapidly adsorbed by the particles. To cool the sensing element 12, the control unit 20 applies current through the thermo-electric module 16 in a selected direction so as to cause the thermo-electric module to draw heat from the sensing element 12 and dissipate said heat into the heat sink 18. When the stratum of particles is substantially at the sensing temperature, the concentration of the substance of interest is measured by measuring the electrical resistance or conductance between the sensor output leads 30,32. The sensing element 12 is then heated in a controlled fashion to a relatively higher purging temperature at which the substance of interest is relatively rapidly desorbed from the particles. The purging temperature of the adsorptive sensing element 12 of the present invention is typically less than 140° F. (60° C.), and thus well below the auto-ignition temperatures of most substances of interest. To heat the sensing element 12, the control unit 20 applies current through the thermo-electric module 16 in an opposite direction so as to cause the thermo-electric module to draw heat from the heat sink 18 and transfer the heat to the sensing element.

The controlled adsorb/purge cycle method of the present invention is best suited to use where the concentration of the substance of interest must be very carefully monitored, and both increases and decreases in concentration must be promptly and accurately detected.

A third contemplated method of operation of a thermo-electrically regulated adsorptive sensing device is well suited to determining the composition of an unknown substance of interest. An adsorptive sensing element displays respectively unique temperature dependent responses for each of many substances. Characteristic, temperature dependent response patterns for many substances can be prepared and stored, and later compared on a matching basis to the response of the sensing element to an unknown substance of interest as the temperature of the sensing element is heated and cooled in a controlled fashion by a thermo-electric module. The use of adsorptive sensing devices for determining the composition of unknown substances of interest offers several advantages over alternative methods of analyzing unknown substances.

It will be appreciated that although specific embodiments of the apparatus and methods of the present invention have been described herein for purposes of illustration, various modifications, adaptations and additions may be made thereto without departing from the spirit and scope of the invention. Accordingly, the scope of the invention shall be determined solely with reference to the following claims.

What is claimed is:

1. Apparatus for sensing liquids, vapors, gases and like substances of interest, comprising:
    (a) a sensing element which exhibits substantial response to adsorption of the substance of interest when the temperature of the is in a lower range, and which purges itself of said adsorbed substance when operated in a temperature range higher than said lower range;
    (b) temperature sensing means for sensing the temperature of the stratum of particles; and
    (c) temperature regulating means for controlled cooling and heating of the stratum of particles, and comprising a thermo-electric module having:
        (i) a source side in thermally conductive contact with the stratum of particles of the sensing device,
        (ii) an opposite sink side, and
        (iii) at least one thermo-electric couple having a first junction in thermally conductive contact with the source side, and a second junction in thermally conductive contact with the sink side.

2. Apparatus as recited in claim 1, wherein the sensing element comprises:
    (i) a base having an electrically non-conductive, non-absorbent resilient surface,
    (ii) a stratum of discrete, exposed, electrically conductive particles adsorbently sensitive to a selected substance of interest, said particles being distributed over said surface such that electrically conductive contact normally exists between adjacent particles substantially fully throughout the stratum of particles, and
    (iii) two sensor output leads in electrically conductive contact with the stratum of particles at separated points thereon.

3. Apparatus as recited in claim 1, further including heat sink means for disposing of heat from the sink side of the thermo-electric element and for replacing heat into said sink side.

4. Apparatus as recited in claim 3, wherein the heat sink means comprises a liquid cooled heat sink having a circulation chamber in thermally conductive contact with the sink side of the thermo-electric module.

5. Apparatus as recited in claim 1, wherein the temperature sensing means comprises a thermistor having a temperature responsive electrical resistance, said thermistor being in thermally conductive contact with the stratum of particles of the sensing device.

6. Apparatus according to claim 1, further including controller means for operating the temperature regulating means so as to maintain the sensing element within no more than about 1° F. above or below a selected temperature.

7. Apparatus according to claim 6, wherein the temperature regulating means comprises a thermo-electric module having:
    (iv) a source side in thermally conductive contact with the stratum of particles of the sensing device,
    (v) an opposite sink side, and
    (vi) at least one thermo-electric couple having a first junction in thermally conductive contact with the source side, and a second junction in thermally conductive contact with the sink side; and
    wherein the controller means applies variable amounts of electrical current through said thermo-electric module.

8. Apparatus according to claim 1, further including controller means for operating the temperature regulating means for controlled heating of the sensing element until the stratum of particles reaches a relatively higher purging temperature at which the substance of interest is relatively rapidly desorbed from the sensing element, and controlled cooling of the stratum of particles until the sensing element reaches a relatively lower sensing temperature at which the substance of interest is relatively rapidly adsorbed by the sensing element.

9. Apparatus according to claim 8, wherein the temperature regulating means comprises a thermo-electric module having:
    (vii) a source side in thermally conductive contact with the stratum of particles of the sensing device, (viii) an opposite sink side, and
(ix) at least one thermo-electric couple having a first junction in thermally conductive contact with the source side, and a second junction in thermally conductive contact with the sink side; and
wherein the controller means applies variable amounts of electrical current through said thermo-electric module.

10. Apparatus according to claim 8, wherein the purging temperature of the sensing element is significantly less than the auto-ignition temperature of the substance of interest.

11. Apparatus according to claim 8, wherein the purging temperature of the sensing element is no more than about 140° F. (60° C.).

12. A method for sensing liquids, vapors, gases and like substances of interest, comprising the steps of:
(a) exposing to a selected substance of interest a sensing element including
  (i) a base having a non-adsorbent, electrically non-conductive surface,
  (ii) a stratum of discrete, exposed, electrically conductive particles adsorbently sensitive to a selected substance of interest, said particles being independently anchored on the surface of the base such that electrically conductive contact normally exists between adjacent particles substantially fully throughout the stratum of particles, and
  (iii) two sensor output leads in electrically conductive contact with the stratum of particles at separated points thereon;
(b) measuring the electrical resistance or conductance between the sensor output leads;
(c) rapid, controlled cooling by electrical heat sink means of the stratum of particles when the temperature of the stratum of particles rises above a selected upper limit temperature; and
(d) rapid, controlled heating by electrical heat source means of the stratum of particles of the sensing device when the temperature of the stratum of particles falls below a selected lower limit temperature.

13. A method as recited in claim 12,
wherein the stratum of particles is cooled by applying an electrical current in a selected direction through a thermo-electric element having a source side in thermally conductive contact with the stratum of particles of the sensing device and an opposite sink side, said current cooling the source side and heating the sink side of the thermo-electric element; and
wherein the stratum of particles is heated by applying an electrical current through the thermo-electric element in an opposite heating direction, said current heating the source side and cooling the sink side of the thermo-electric element.

14. A method for sensing liquids, vapors, gases and like substances of interest, comprising the steps of:
(a) exposing to a selected substance of interest a sensing element including
  (i) a base having a non-adsorbent, electrically non-conductive resilient surface,
  (ii) a stratum of discrete, exposed, electrically conductive particles adsorbently sensitive to a selected substance of interest, said particles being independently anchored on the surface of the base such that electrically conductive contact normally exists between adjacent particles substantially fully throughout the stratum of particles, and
  (iii) two sensor output leads in electrically conductive contact with the stratum of particles at separated points thereon;
(b) rapid, controlled heating by electrical heat source means of the stratum of particles until the stratum of particles reaches a relatively higher purging temperature at which the substance of interest is relatively rapidly desorbed from said particles;
(c) rapid, controlled cooling by electrical heat sink means of the stratum of particles until the stratum of particles reaches a relatively lower sensing temperature at which the substance of interest is relatively rapidly adsorbed by said particles; and
(d) measuring the electrical resistance or conductance between the sensor output leads when the stratum of particles is substantially at the sensing temperature.

15. A method as recited in claim 14, wherein the stratum of particles is cooled by applying an electrical current in a selected direction through a thermo-electric element having a source side in thermally conductive contact with the stratum of particles of the sensing device and an opposite sink side, said current cooling the source side and heating the sink side of the thermo-electric element; and
wherein the stratum of particles is heated by applying an electrical current through the thermo-electric element in an opposite heating direction, said current heating the source side and cooling the sink side of the thermo-electric element.

* * * * *